(12) United States Patent
Madabhushi et al.

(10) Patent No.: US 9,177,105 B2
(45) Date of Patent: Nov. 3, 2015

(54) QUANTITATIVELY CHARACTERIZING DISEASE MORPHOLOGY WITH CO-OCCURRING GLAND TENSORS IN LOCALIZED SUBGRAPHS

(71) Applicant: Case Western Reserve University, Cleveland, OH (US)

(72) Inventors: Anant Madabhushi, Beachwood, OH (US); George Lee, Parlin, NJ (US); Sahirzeeshan Ali, Houston, TX (US); Rachel Sparks, Seattle, WA (US)

( * ) Notice: Subject to any disclaimer, the term of this patent is extended or adjusted under 35 U.S.C. 154(b) by 84 days.

(21) Appl. No.: 14/226,083

(22) Filed: Mar. 26, 2014

(65) Prior Publication Data

US 2014/0294264 A1    Oct. 2, 2014

Related U.S. Application Data

(60) Provisional application No. 61/806,578, filed on Mar. 29, 2013.

(51) Int. Cl.

| | |
|---|---|
| G06K 9/00 | (2006.01) |
| G06F 19/00 | (2011.01) |
| G06T 7/00 | (2006.01) |
| G01R 33/56 | (2006.01) |
| G06K 9/46 | (2006.01) |
| G06K 9/62 | (2006.01) |

(52) U.S. Cl.
CPC .......... *G06F 19/321* (2013.01); *G01R 33/5608* (2013.01); *G06F 19/3431* (2013.01); *G06K 9/0014* (2013.01); *G06K 9/00147* (2013.01); *G06K 9/4671* (2013.01); *G06K 9/6256* (2013.01); *G06T 7/0014* (2013.01); *G06T 7/0032* (2013.01); *G06T 7/0083* (2013.01); *G06T 7/0087* (2013.01); *G06T 2207/30081* (2013.01)

(58) Field of Classification Search
CPC .................................. G06F 19/00; G06T 7/00
USPC .......................................................... 382/128
See application file for complete search history.

(56) References Cited

U.S. PATENT DOCUMENTS

| | | | | |
|---|---|---|---|---|
| 2007/0249929 | A1* | 10/2007 | Jeong et al. .................... | 600/410 |
| 2011/0199084 | A1* | 8/2011 | Hasan .......................... | 324/309 |
| 2012/0195480 | A1* | 8/2012 | Gonz lez Penedo et al. . | 382/128 |
| 2014/0233826 | A1* | 8/2014 | Agaian et al. ................. | 382/133 |
| 2015/0216496 | A1* | 8/2015 | Lee et al. ...................... | 600/425 |

* cited by examiner

Primary Examiner — Gregory F Cunningham (57) ABSTRACT

Apparatus, methods, and other embodiments associated with objectively predicting biochemical recurrence with co-occurring gland tensors in localized subgraphs are described. One example apparatus includes a set of logics that associate directional disorder with a risk of failure in a material. A first logic detects a fundamental unit of composition in the material, segments boundaries of the fundamental unit, and calculates a directional tensor for the fundamental unit. A second logic constructs a localized sparsified subgraph whose nodes represent centroids of the fundamental units, defines pairwise spatial relationships between the fundamental units, and constructs a directional co-occurrence matrix based on the spatial relationships. A third logic derives second order statistical features from the co-occurrence matrix, and produces a risk failure score as a function of the second order statistical features. The second order statistical features include the entropy of the directional organization of the fundamental units.

24 Claims, 6 Drawing Sheets

QUANTITATIVELY CHARACTERIZING DISEASE MORPHOLOGY WITH CO-OCCURRING GLAND TENSORS IN LOCALIZED SUBGRAPHS

CROSS REFERENCE TO RELATED APPLICATIONS

This application claims the benefit of U.S. Provisional Application No. 61/806,578 filed on Mar. 29, 2013.

BACKGROUND

Thousands of men diagnosed with prostate cancer (CaP) in the United States undergo radical prostatectomy (RP) each year. For a significant proportion of these patients, biochemical recurrence (BCR) of the prostate cancer occurs within five years of surgery. Consequently, detecting BCR shortly after surgery may facilitate determining whether other treatments are necessary, and, if necessary, are initiated. Gleason scoring is a pathological grading system based on visual analysis by a pathologist of glandular and nuclear morphology. Gleason scoring is currently regarded as the best biomarker for predicting CaP aggressiveness and long-term post-surgical patient outcome. However, the post-surgical outcome of CaP patients with the same intermediate Gleason scores can vary significantly. Furthermore, Gleason scoring is subjective and is, therefore, susceptible to considerable inter-reviewer variability. Due to these limitations of Gleason scoring, other post-operative nomograms have been developed for predicting CaP aggressiveness and long-term post-surgical patient outcome.

Conventional nomograms may incorporate additional clinical variables to assist in predicting CaP aggressiveness and long-term post-surgical patient outcome. For example, tumor stage, pre-operative prostate specific antigen (PSA), and positive surgical margins have been integrated into the Kattan nomogram by Kattan et al., Postoperative nomogram for disease recurrence after radical prostatectomy for prostate cancer, J. Clinical Oncology, 17(5): 1499-1499, 1999. The Han Tables use the Gleason sum, tumor stage, and pre-operative PSA to construct a series of probability tables. Han et al., Biochemical (prostate specific antigen) recurrence probability following radical prostatectomy for clinically localized prostate cancer, J. Urol, 169(2):517-523, February 2003. Adding the date of surgery to a nomogram as a prognostic variable was described by Stephenson et al., in J. Clinical Oncology, 23(28):7005-7012, 2005. CARPA, developed at the University of California at San Francisco, separates post-operative CaP patients into risk categories and incorporates the percentage of positive biopsy cores into its risk assessment. Cooperberg et al., Multi-institutional validation of the UCSF cancer of the prostate risk assessment for prediction of recurrence after radical prostatectomy, Cancer, 107(10): 2384-2391, 2006. The Memorial Sloan Kettering Cancer Center (MS-KCC) nomogram incorporates age and time free of cancer. Hinev et al., Validation of pre- and postoperative nomograms used to predict the pathological stage and prostate cancer recurrence after radical prostatectomy: a multi-institutional study, J. BU ON.: official journal of the Balkan Union of Oncology, 16(2):316, 2011. These conventional nomograms all rely on Gleason scoring, and consequently suffer from the inter-reviewer variability and subjectivity that affects the predictive value of Gleason scoring.

The advent of digital whole-slide scanners has allowed the digitization of tissue slides. Digitized slide images have been subjected to quantitative histomorphometry (QH), which applies computational tools to describe, classify, and diagnose disease patterns from the images. However, QH has conventionally been modeled after pathological Gleason grading. For example, morphological descriptors including gland size and perimeter ratio have been used in automated grading systems to distinguish between benign and malignant regions. Similarly, image texture has been used to characterize the appearance of CaP morphology. Extracting second-order image intensity texture features from co-occurrence matrices was described in Jafari-Khouzani et. al., Multiwavelet grading of pathological images of prostate, IEEE Trans on Biomedical Engineering, 50(6):697-704, 2003. Co-occurrence matrices have been used to evaluate the frequency with which two image intensities appear within a pre-defined distance of each other within a region of interest. First and second-order statistical features can be extracted to describe the local image texture. Haralick et al., Textural features for image classification, IEEE Trans on Systems, Man and Cybernetics, 3(6):610-621, 1973. For example, U.S. Pat. No. 8,634,610 disclosed a probabilistic assessment determined through the use of a logistic regression model based on a texture analysis of an image of a region of interest. However, texture features may suffer from a lack of transparency and interpretability.

Attempts to model CaP appearance have used the spatial arrangement of individual nuclei and glands. Color, texture, and structural morphology have been used to perform automated Gleason scoring, while nuclear roundness variance has been used to predict BCR. Graph networks have also been used to characterize the spatial arrangement of nuclei and glands. For example, using Voronoi and Delaunay-based graph tessellations to describe tissue architecture in CaP histology is described by Christens-Barry and Partin, Quantitative grading of tissue and nuclei in prostate cancer for prognosis prediction, Johns Hopkins Apl. Technical Digest, 18:226-233, 1997. Minimum spanning trees have been shown to strongly correlate with Gleason scoring by Doyle et al., Cascaded discrimination of normal, abnormal, and confounder classes in histopathology: Gleason grading of prostate cancer, BMC bioinformatics, 13(1):282, 2012. However, these conventional techniques all rely on fully connected graphs in which nuclei embedded in stromal and epithelial regions are connected in the graphs. This connecting of stromal and epithelial nuclei results in features extracted from conventional graphs representing averaged attributes of both stromal and epithelial regions. Unfortunately, such fully connected graphs are not sensitive to local glandular organization. Thus, while conventional methods for predicting BCR in prostate cancer patients have incorporated additional clinical variables, utilized QH, and explored image textures and fully-connected graphs to assist in predicting CaP aggressiveness, conventional methods still suffer from the drawbacks of those techniques.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Conventional systems for predicting BCR in CaP patients that rely on Gleason scoring suffer from inter-reviewer variability that affects the accuracy of their predictions. Example apparatus and methods utilize the directionality of glands to associate disorder in gland orientations with malignancy and risk of post-surgical biochemical recurrence in CaP patients. Example apparatus and methods employ co-occurring gland tensors to capture the directionality of glands. Example apparatus and methods employ co-occurring gland tensor matrices to derive second-order statistical features related to the orientations of glands in a localized gland network. Prostate and other glands exhibit different degrees of orientation disorder as a function of malignancy. Therefore, the described apparatus and methods objectively distinguish malignant tissue from benign tissue, and objectively distinguish patients who may or may not experience BCR.

Prostate cancer may be considered a disease of glandular disorder. Normal benign glands align themselves with respect to the fibro muscular stroma, and thereby display a coherent directionality. In benign or less aggressive prostate cancer, gland orientations within local neighborhoods are similar to each other. Malignant prostate glands lose their capability to orient themselves and consequently display no preferred directionality. In more aggressive disease, gland orientations are dissimilar. As the degree of malignancy increases, and as the degree of aggressiveness of the disease increases, the coherence of the gland orientations within localized regions becomes more disorganized, and may be completely disrupted. This disorganization of gland orientations, which may be expressed as the entropy of gland orientations, varies as a function of malignancy.

Quantitative histomorphometry applies advanced computational image analysis to reproducibly and automatically describe disease appearance on digitized histopathology images. Conventionally, QH features have been modelled after pathological Gleason grades. Gleason scoring is a qualitative system in which a pathologist uses tissue morphology to assess CaP aggressiveness. A pathologist may use morphological descriptors such as gland size and perimeter ratio to assign a Gleason score, where a lower score (e.g. 2), is associated with more favorable longer term prognosis, and a higher score (e.g. 10), is associated with a less favorable longer term prognosis. Conventional Gleason scoring therefore suffers from inter-reviewer variability, especially around intermediate Gleason scores (e.g., 7). Different patients with identical intermediate Gleason scores may exhibit radically different longer term outcomes. Example apparatus and methods facilitate distinguishing outcomes for patients with identical Gleason scores.

QH tissue architecture has been modeled using graph networks to characterize the spatial arrangement of nuclei and glands. Voronoi and Delaunay features have been used to describe the architecture of various structures in CaP histology. For example, minimum spanning trees, in addition to Voronoi and Delaunay features, have been shown to be strong predictors of Gleason score. Conventional implementations of Voronoi and Delaunay features with minimum spanning trees, are, however, derived from fully connected graphs. Fully connected graphs are not sensitive to local glandular orientation. Nuclei embedded within stromal and epithelial regions are connected in fully connected graphs. The graph edges in these fully connected graphs will traverse the epithelial-stromal interfaces and regions. Consequently, the features extracted from conventional fully connected graphs represent averaged attributes of both stromal and epithelial architecture.

Example apparatus and methods employ co-occurring gland tensors (CGT) as a quantitative histomorphometric feature to capture the directional information in localized gland networks to characterize differences in gland orientations. These differences facilitate distinguishing between benign tissue regions and malignant tissue regions, and between CaP patients who may or may not experience BCR following radical prostatectomy. Example apparatus and methods facilitate predicting BCR for intermediate-risk prostate cancer patients while improving on the limitations of conventional Gleason scoring and other post-operative nomograms.

Example apparatus and methods individually segment gland boundaries from digitized pathology sections. A tensor is assigned to each detected gland. The assigned tensor represents the dominant orientation of the gland based off the major axis of the gland. A subgraph is then constructed where the nodes of the subgraph represent the centroids of glands. The subgraph links together glands proximal to each other into a localized gland network. The subgraph of the localized gland network characterizes the local gland arrangement. Unlike conventional implementations of Voronoi and Delaunay features with minimum spanning trees, the subgraph of the localized gland network prevents subgraph edges from traversing heterogeneous tissue regions such as stroma and epithelium. Since the subgraphs are localized and limited to the epithelial regions, the contributions from the stromal regions are minimized.

Example apparatus and methods employ co-occurrence matrices to capture second-order statistics of gland orientations within localized gland networks in the digitized image. A co-occurrence matrix captures the frequency with which orientations of two glands proximal to each other co-occur. Co-occurrence features, including entropy, are extracted from the co-occurrence matrix associated with localized gland networks, which may also be referred to as neighborhoods. The extracted co-occurrence features capture the degree to which gland orientations are similar or divergent to each other within the localized gland network. A localized gland network, or neighborhood, with a high entropy value would reflect a high degree of disorder among gland orientations. A low entropy value indicates that the gland tensors are likely to be aligned roughly in the same direction within the neighborhood or localized network.

Example apparatus and methods automatically detect and segment glandular boundaries on the histological image. Example apparatus and methods employ automatic region-growing gland segmentation. Segmentation is performed using the luminance channel in Commission internationale de l'éclairage L*a*b* (CIELAB) color space. In the luminance channel, glands appear as contiguous, high intensity pixel regions bordered by sharp edges as boundaries. In one example, the luminance channel image is convolved with a Gaussian kernel. The luminance channel image is convolved with the Gaussian kernel at multiple scales $\sigma_g \in \{0.025, 0.05, 0.1, 0.2\}$ mm to account for multiple gland sizes. The pixels that represent peaks or maxima of the resulting smoothed convolved luminance images are used as seed pixels for the region growing procedure. In one example, a $12\sigma_g \times 12\sigma_g$ bounding box is initialized around initial seed pixels. The seed pixels represent the current region (CR). A number (e.g., 8) of connected pixels surrounding the CR are denoted as the current boundary (CB). The pixel in the CB with the highest intensity is removed from the CB and this removed CB pixel is incorporated into the CR. Of the surrounding pixels of the new CR pixel, those pixels not already in the CR are then incorporated into the CB. The boundary strength is identified iteratively. The internal boundary (IB) is defined as all CR pixels adjacent to the CB. Boundary strength is defined as the mean intensity of the pixels in the IB minus the mean intensity of the pixels in the CB. Processing terminates when a pixel outside the bounding box is about to be added. The optimal region is defined as the region CR at the iteration at which the maximum boundary strength was achieved. Overlapping regions may be resolved by removing the region with the lowest boundary strength.

Example apparatus and methods define pairwise spatial relationships between glands with sparsified graphs. In one example, a graph $G=\{V,E\}$, is used to define a flexible localized neighborhood. In graph G, V represents the set of n gland centroids $\gamma_i, \gamma_j \in V$, $i, j \in \{1, 2, \ldots, n\}$ as nodes, and E represents the set of edges that connect the nodes. The edges between pairs of nodes $\gamma_i, \gamma_j$ are set as a probabilistic decaying function of the Euclidean distance $$E = \{(i,j) : r < d(i,j)^{-\alpha}, \forall \gamma_i, \gamma_j \in V\}$$

where $d(i,j)$ represents the Euclidean distance between $\gamma_i$ and $\gamma_j$. The density of the graph is controlled by $\alpha \geq 0$ where $\alpha$ approaching 0 represents a high probability of connecting nodes while $\alpha$ approaching infinity represents a low probability of connecting nodes. $r \in [0, 1]$ is generated by a random number generator.

Example apparatus and methods perform principal component analysis (PCA) to determine the directionality of glands. For a gland $\gamma_p$, PCA is performed on a set of boundary points $[x_p, y_p]$ to obtain the principal components $A=[a_1, a_2]$. The first principal component $a_1$ describes the directionality of the gland in the form of the major axis. One of ordinary skill in the art would appreciate that the greatest variance in the gland boundary occurs along the major axis. The major axis $a_1$ is then converted to an angle $\theta(\gamma_p) \in [0°, 180°]$ counter-clockwise from the horizontal vector $\langle 1, 0 \rangle$.

Example apparatus and methods employ co-occurring gland tensor (CGT) matrices to capture similarities within local gland neighborhoods. Conventional systems use co-occurrence matrices to describe texture features. In conventional systems, gray-level intensity values are analyzed within a range of neighborhoods. Conventionally, texture features described by co-occurrence matrices frequently suffer from a lack of transparency and interpretability. In contrast, example apparatus and methods use co-occurrence matrices to capture local similarities in gland tensors, rather than merely using co-occurrence matrices to describe texture features. To compute angle similarities, the angle $\theta(\gamma_p)$ is discretized such that $\bar{\theta}(\gamma_p) = \omega * \text{floor}(\theta/\omega)$ where $\omega$ is a discretization factor. In one embodiment, $\omega$ is set to 10, which allows angles to be discretized every 10 degrees. In other embodiments, $\omega$ may be set to other values, allowing angles to be discretized or binned within other intervals. Discretization facilitates regarding glands with directionalities contained within the "bin" as having substantially similar orientations.

For a gland $\gamma_i \in V$, example apparatus and methods define a neighborhood $N_p$ to include all $\gamma_j \in V$ where a path between $\gamma_i$ and $\gamma_j$ exists in graph G. Example systems and methods define a $b \times b$ co-occurrence matrix C, where b is the number of discrete angular bins, such that for the neighborhood $N_p$, $$C_{N_p}(\bar{\theta}_1, \bar{\theta}_2) \underset{\gamma_i, \gamma_j \in N_p}{=} \sum_{\substack{\theta_1, \theta_2 = 1 \\ \theta_1 \neq \theta_2}}^{b} \begin{cases} 1, & \text{if } \theta(\gamma_i) = \theta_1 \text{ and } \theta(\gamma_j) = \theta_2, \\ 0, & \text{otherwise} \end{cases}$$

where $$b = \frac{180}{\omega}.$$

$C_{N_p}(\bar{\theta}_1, \bar{\theta}_2)$ are aggregated such that $$C(\bar{\theta}_1, \bar{\theta}_2) = \frac{1}{n} \sum_{p=1}^{n} C_{N_p}(\bar{\theta}_1, \bar{\theta}_2).$$

Example apparatus and methods extract second-order statistical features from the CGT matrices. In one embodiment, the second-order statistical features entropy, homogeneity, energy, and correlation are extracted from the co-occurrence matrix. In this example, entropy may be defined as $\Sigma_{\theta_1, \theta_2} -C(\theta_1, \theta_2) \log(C(\theta_1, \theta_2))$. Homogeneity may be defined as $$\Sigma_{\theta_1, \theta_2} \frac{C(\theta_1, \theta_2)}{1 + |\theta_1 - \theta_2|}.$$

Energy may be defined as $\Sigma_{\theta_1, \theta_2} C(\theta_1, \theta_2)^2$. Correlation may be defined as $$\Sigma_{\theta_1, \theta_2} \frac{(\theta_1 - \mu_{\theta_1})(\theta_2 - \mu_{\theta_2}) C(\theta_1, \theta_2)}{\sigma_{\theta_1}, \sigma_{\theta_2}}.$$

In other embodiments, other second-order statistical features may be extracted from each tensor co-occurrence matrix. Other second-order statistical features may include contrast energy, contrast inverse moment, contrast average, contrast variance, contrast entropy, intensity average, intensity variance, and intensity entropy. By using second-order statistical features derived from the CGT matrices, example apparatus and methods offer a statistically significant improvement in distinguishing cancerous from non-cancerous tissue regions, and in predicting BCR, compared to conventional QH.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 1:
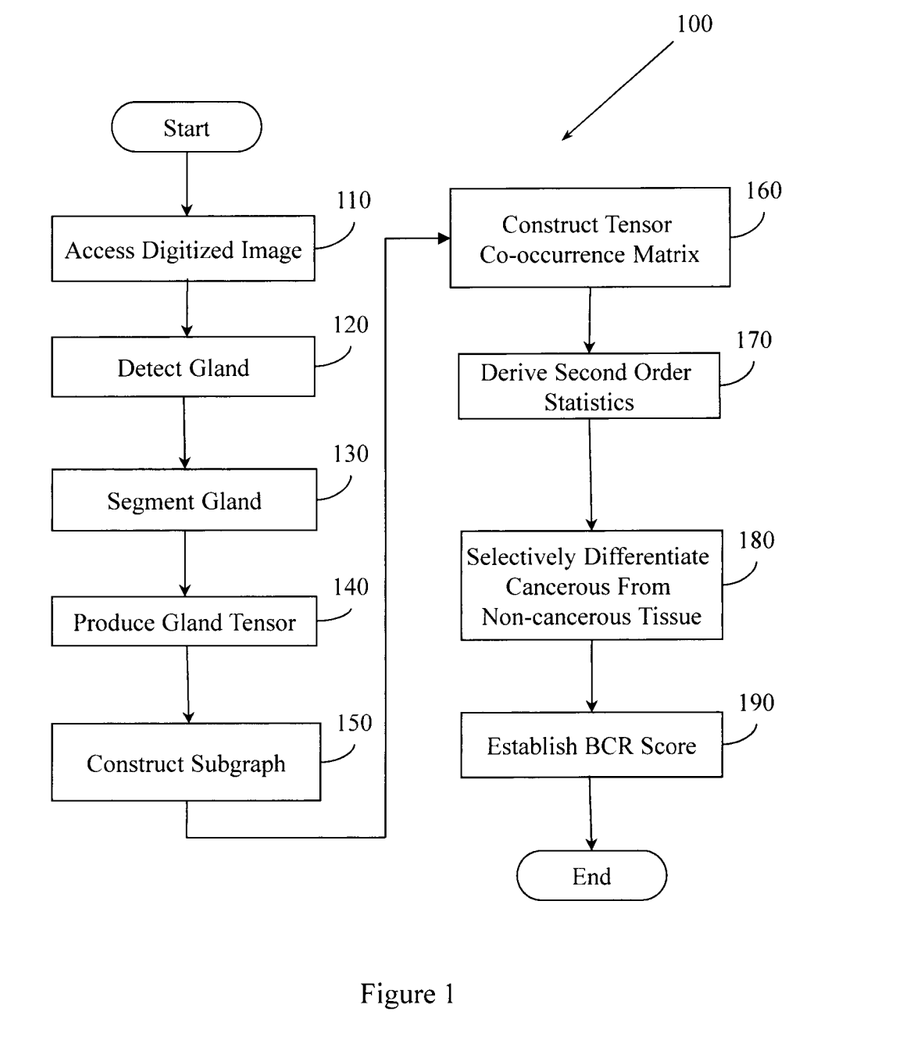
FIG. 1 illustrates an example method of associating gland orientation disorder with malignancy and risk of post-surgical biochemical recurrence (BCR) in a prostate cancer (CaP) patient.

FIG. 1 illustrates a computerized method 100 of associating gland orientation disorder with malignancy and risk of post-surgical biochemical recurrence in a CaP patient. Method 100 includes, at 110, accessing a digitized image of a section of a prostate demonstrating pathology associated with CaP in a patient. Accessing the digitized image may include, for example, acquiring data from a medical imaging apparatus, receiving data via a computer network, receiving data through a function call, or other computer based operation. In one embodiment, prostate excised after RP may be sectioned, stained, and digitized at a resolution of 0.5 µm per pixel using a whole slide scanner. In other embodiments, different resolutions may be used when digitizing the excised prostate. For a digitized image, CaP in a region may be annotated by a pathologist.

Method 100 also includes, at 120, detecting a gland in a region of interest in the digitized image. In one embodiment, detecting a gland in the region of interest may include automatic region growing. One method of automatic region growing is described in US 2011-0243417 A1. One of ordinary skill in the art will appreciate that other embodiments may employ other methods of detecting a gland in a region of interest in the digitized image.

Method 100 also includes, at 130, segmenting an individual gland boundary in the region of interest in the digitized image into a set of gland boundary points. In one embodiment, segmenting is performed by automatic region-growing. Segmentation may be performed using the luminance channel in CIELAB color space. In another embodiment, color spaces other than CIELAB that include a luminance channel may be used. In another embodiment, method 100 includes using a probabilistic pair-wise Markov random field classifier to remove a non-gland boundary in the region of interest. In another embodiment, other methods may be used to remove non-gland boundaries in the region of interest.

Method 100 also includes, at 140, producing a gland tensor by associating a tensor with the gland. The gland tensor indicates the dominant orientation of the gland, and the gland tensor may be based on the major axis of the gland. In one embodiment, the dominant orientation of the gland is obtained through principal component analysis of the set of gland boundary points. The first principal component describes the directionality of the gland in the form of the major axis. The greatest variance in the gland boundary occurs along the major axis. In another embodiment, the dominant orientation of the gland may be obtained through other methods. In one embodiment, method 100 converts the major axis to an angle counterclockwise from a positive horizontal axis. For example, method 100 may convert the major axis to an angle $\theta(\gamma_p) \in [0°, 180°]$ counterclockwise from the vector $<1, 0>$. In another embodiment, the angle $\theta(\gamma_p)$ may be computed from a different vector, in a different direction, or within a different co-ordinate system. In one embodiment, method 100 also includes discretizing gland orientations. For example, the angle $\theta(\gamma_p)$ may discretized such that $$\overline{\theta}(\gamma_p) = \omega * \mathrm{floor}\left(\frac{\theta}{\omega}\right)$$

where $\omega$ is a discretization factor. In another embodiment, the discretization factor $\omega$ may be 10, which would discretize the angles into bins of ten degrees. In another embodiment, the discretization factor $\omega$ may be a value other than 10, which would discretize the angles into different sized bins.

Method 100 also includes, at 150, constructing a subgraph of a localized gland network within the region of interest. Constructing the subgraph comprises linking individual glands located proximal to each other into the localized gland network, where the nodes of the subgraph represent individual gland centroids, and where the edges of the subgraph are defined between pairs of glands by a probabilistic decaying function. Constructing a localized subgraph facilitates characterization of local gland arrangement, and prevents subgraph edges from traversing heterogeneous tissue regions including stroma and epithelium, thereby improving on conventional methods. Preventing graph edges from traversing heterogeneous tissue regions including stroma and epithelium eliminates noise from the regions that separate the glandular regions. In one embodiment, the subgraph is a sparsified graph, where the sparsified graph defines a pairwise spatial relationship between the glands. In one embodiment, the probabilistic decaying function is a probabilistic decaying function of the Euclidean distance between gland centroids. In another embodiment, a different probabilistic decaying function may be used to define the edges of the subgraph. In one embodiment, the density of the subgraph is controlled by a randomly generated value V, where V is a real number. V may range from 0 through infinity, where 0 represents a high probability of connecting nodes, and infinity represents a low probability of connecting nodes.

Method 100 also includes, at 160, constructing a tensor co-occurrence matrix. In one embodiment, elements of the tensor co-occurrence matrix comprise gland tensor pairs, where the gland tensor pairs are defined by the subgraph. The tensor co-occurrence matrix aggregates co-occurring gland tensors based, at least in part, on the frequency with which orientations of two individual glands located proximal to each other co-occur. In contrast to conventional systems that analyze first-order statistics, the co-occurring gland tensor features are able to implicitly capture the cyclical properties of gland orientation. Co-occurring gland tensors introduce more biological information compared to conventional texture features, which focus only on grayscale pixel intensity. Consequently, higher classification accuracy is achieved compared to conventional methods. In one embodiment, CGT features facilitate achieving a BCR prediction classification accuracy of 66%. In contrast, conventional methods of predicting BCR, using texture, gland morphology, Voronoi graphs, Delaunay graphs, and minimum spanning trees achieve at best a 55% classification accuracy.

Method 100 also includes, at 170, deriving second-order statistics of gland orientations in the localized gland networks in the digitized image. In one embodiment, the second-order statistics include entropy, homogeneity, energy, correlation, contrast energy, contrast inverse moment, contrast average, contrast variance, contrast entropy, intensity average, intensity variance, or intensity entropy. In another embodiment, other second-order statistics may be derived. Different combinations of second-order statistics may be employed.

Method 100 also includes, at 180, selectively differentiating a cancerous tissue region from a non-cancerous tissue region in the image based, at least in part, on the second-order statistics. In one example, a heatmap of the co-occurrence matrices of the region of interest is generated, and areas of similar gland tensors are displayed in similar colors. The colors may pertain to gland orientations from 0° to 180°. For example, the heatmap may denote the frequency with which two glands of different directionalities co-occur in each neighborhood. A first color may indicate low co-occurrence and a second color may indicate high co-occurrence.

Method 100 also includes, at 190, establishing a BCR score for the patient based, at least in part, on the second-order statistics. In one embodiment, the mean, standard deviation, and range of the second-order statistics are calculated, yielding a set F of CGT features. F may be used to train a classifier to distinguish between categories of interest, and the classifier used to assign each region of interest into classes {+1, -1} based on the task of distinguishing BCR patients from non-recurrence patients. Predicting BCR in CaP patients using method 100 results in a statistically significant improvement over conventional nomograms and conventional QH features.

While FIG. 1 illustrates various actions occurring in serial, it is to be appreciated that various actions illustrated in FIG. 1 could occur substantially in parallel. By way of illustration, a first process could segment individual gland boundaries, a second process could produce a gland tensor, and a third process could construct a subgraph of a localized gland network. While three processes are described, it is to be appreciated that a greater or lesser number of processes could be employed and that lightweight processes, regular processes, threads, and other approaches could be employed.

Figure 2:
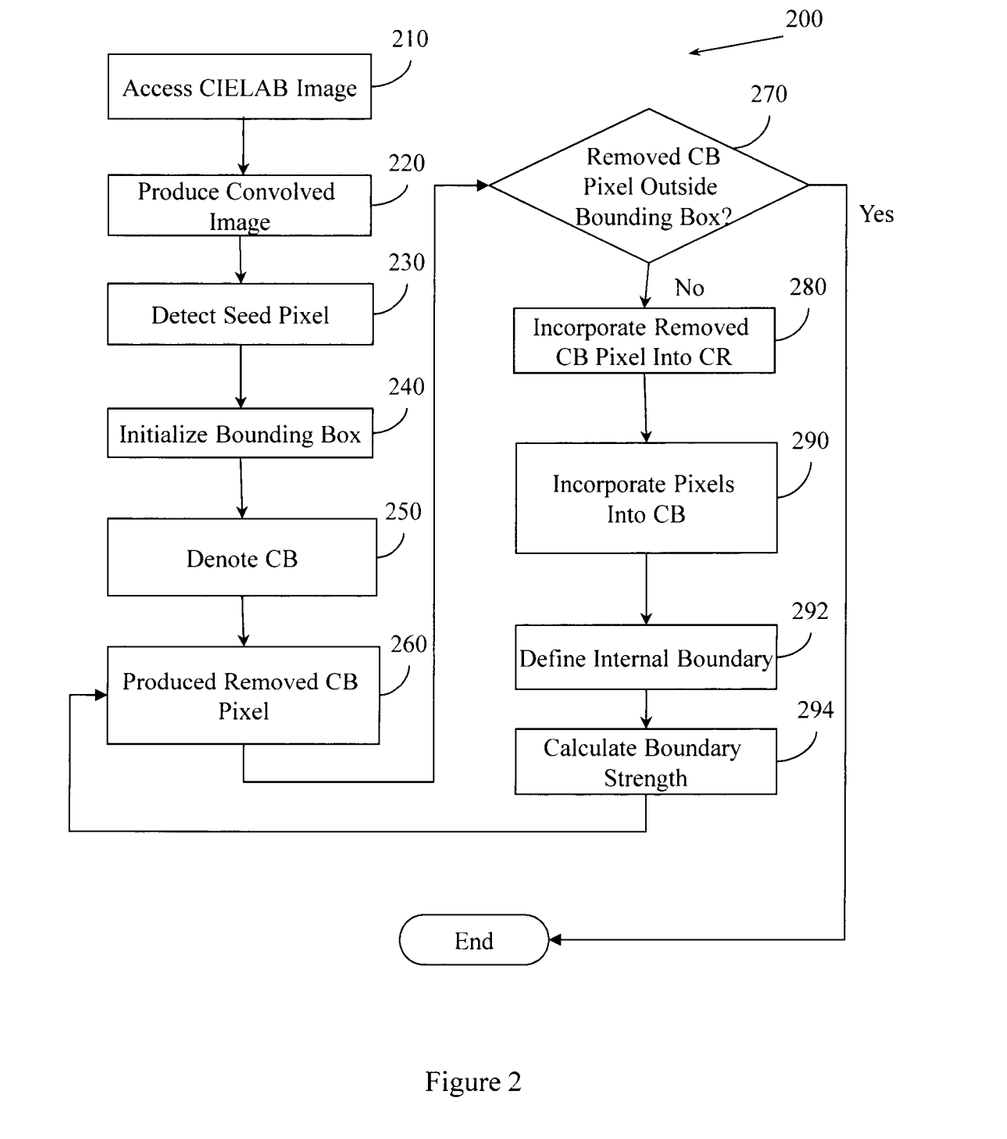
FIG. 2 illustrates an example method associated with detecting a gland and segmenting an individual gland boundary.

FIG. 2 illustrates an embodiment of a computerized method 200 for detecting a gland and segmenting an individual gland boundary. Method 200 includes, at 210, controlling the computer to access a color space luminance channel image of the region of interest. Glands in the color space luminance channel image may appear as contiguous, high intensity pixel regions. In one embodiment, the color space luminance channel image may be in CIELAB color space. In another embodiment, color spaces other than CIELAB that include a luminance channel may be used.

Method 200 also includes, at 220, controlling the computer to produce a convolved luminance image by convolving a color space luminance channel image with a Gaussian kernel. In one embodiment, to account for multiple gland sizes, the luminance image is convolved with the Gaussian kernel at multiple scales, e.g. $\sigma_g \in \{0.025, 0.05, 0.1, 0.2\}$ mm. In another embodiment, other scales may be employed.

Method 200 also includes, at 230, detecting a seed pixel corresponding to a peak intensity in the convolved luminance image. Detecting the maxima within the convolved luminance image facilitates using the detected pixels as seeds for automatic region growing. The seed pixel represents a current region (CR).

Method 200 also includes, at 240, controlling the computer to initialize a bounding box around the seed pixels detected at step 230. In one embodiment, the dimensions of the bounding box are $12\sigma_g \times 12\sigma_g$. In another embodiment, the bounding box may be defined by other dimensions.

Method 200 also includes, at 250, denoting eight connected pixels surrounding the seed pixel as a current boundary (CB). In another embodiment, the number of connected pixels surrounding the seed pixel may be a number other than eight. In one embodiment, method 200 also includes, at 260, producing a removed CB pixel by removing the pixel in the CB with the highest intensity from the CB.

Method 200 also includes, at 270, controlling the computer to determine if the removed CB pixel is not outside the bounding box. If the removed pixel is not outside the bounding box, method 200 continues, at 280, to incorporate the removed CB pixel into the CR as a new CR pixel, and at 290, to incorporate the eight connected pixels surrounding the new CR pixel not already in the CR into the CB. Method 200 then proceeds, at 292, to define an internal boundary (IB) as all CR pixels adjacent to the CB. Method 200 also includes, at 294, defining a boundary strength as the mean intensity of the pixels in the IB minus the mean intensity of the pixels in the CB. If the determination at 270 is that the removed CB pixel is outside the bounding box, method 200 terminates.

Figure 3:
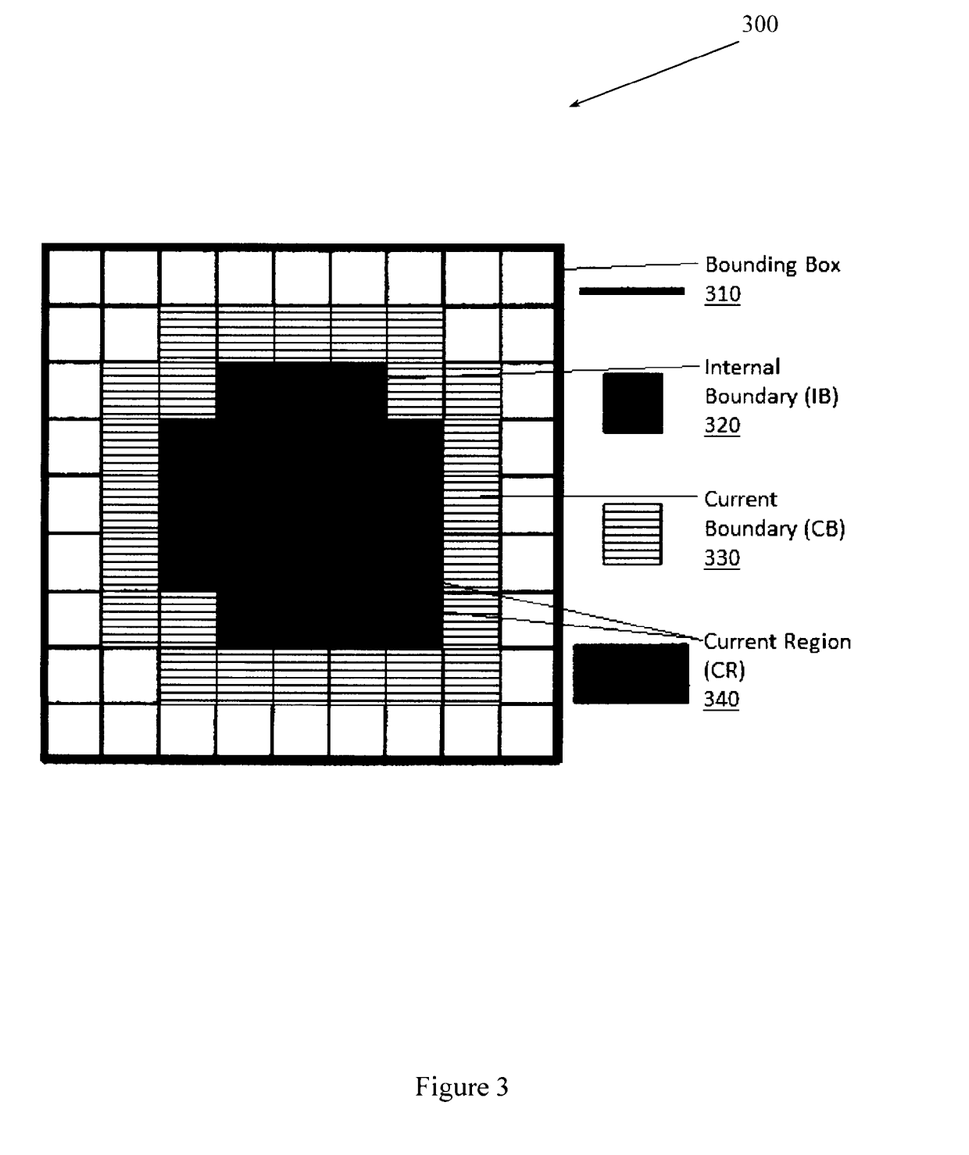
FIG. 3 illustrates a schematic of an iteration of a method for detecting a gland and segmenting an individual gland boundary.

FIG. 3 illustrates a schematic diagram 300 of an iteration of one embodiment of method 200. In FIG. 3, 81 pixels are shown enclosed by a bounding box 310, with the IB 320, CB 330, and CR 340 pixels denoted by the different patterns indicated in the legend.

Figure 4:
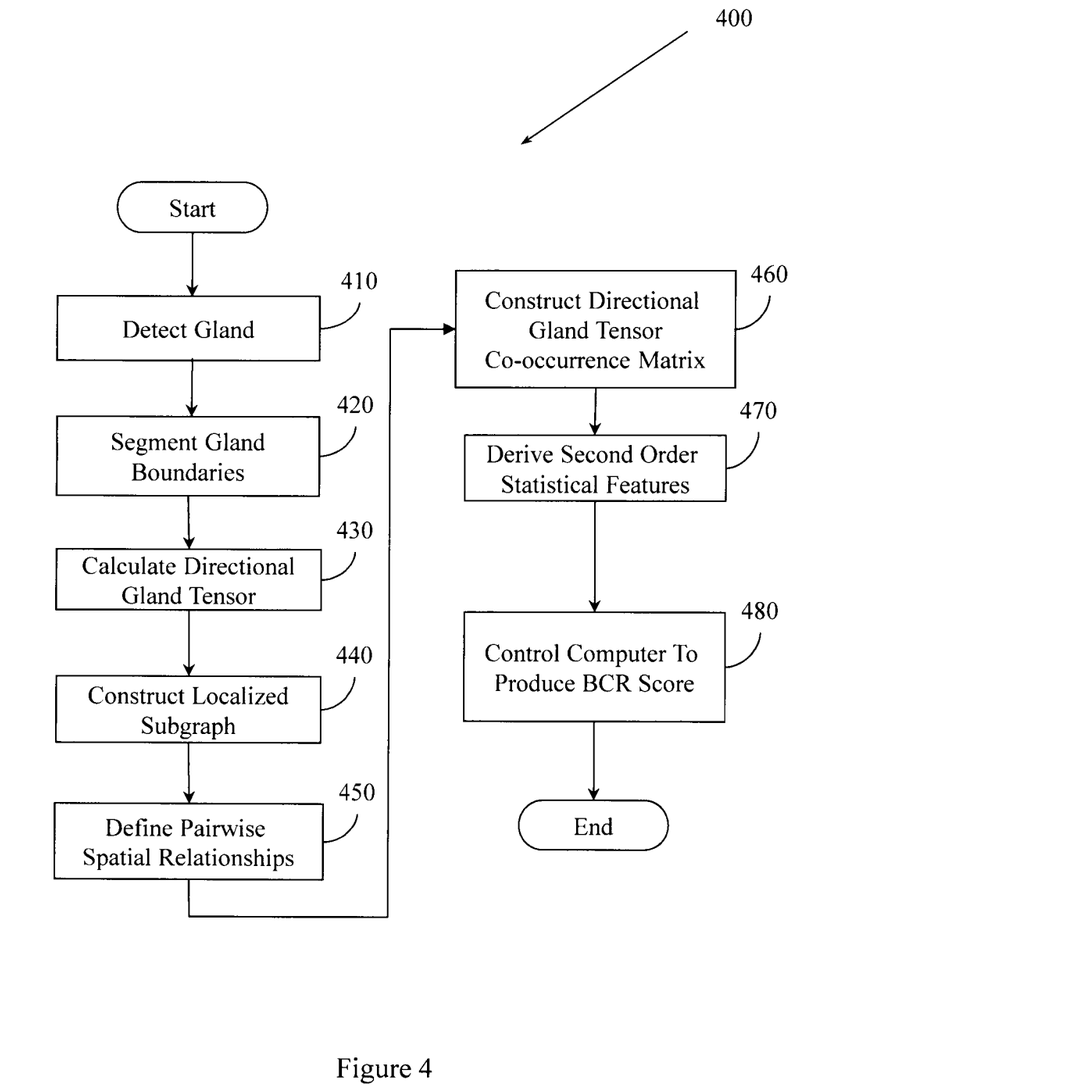
FIG. 4 illustrates an example method associated with controlling a computer to compute an objective BCR score for a cancer patient.

FIG. 4 illustrates a method 400 for controlling a computer to compute a biochemical recurrence score for a cancer patient. Method 400 includes, at 410 detecting a gland in a region of interest of a digitized histopathology section associated with the cancer patient. In one embodiment, the gland is a prostate gland. In another embodiment, the gland is located in tissue other than prostate tissue, (e.g., in breast tissue). One of ordinary skill in the art will appreciate that method 400 may thus compute a biochemical recurrence score for a cancer patient diagnosed with other types of cancer that afflict glandular tissue. Method 400 also includes, at 420, segmenting gland boundaries of the gland into a set of gland boundaries. In one embodiment, method 400 detects the gland using automatic region growing, and segments the gland boundaries using automatic region growing. One of ordinary skill in the art will appreciate that in another embodiment, techniques other than automatic region growing may be employed to detect and segment gland boundaries.

Method 400 also includes, at 430, controlling the computer to calculate a directional gland tensor for the gland. In one embodiment, method 400 calculates the directional gland tensor from a principal component analysis of the set of gland boundaries. The first principal component describes the directionality of the gland in the form of the major axis along which the greatest variance occurs. The principal axis is then converted to an angle calculated counterclockwise from a positive horizontal axis. In another embodiment, method 400 may calculate the directional gland tensor using a technique other than principal component analysis.

Method 400 also includes, at 440, constructing a localized subgraph of a gland network in the region of interest. In one embodiment, the localized subgraph is a cluster graph. The nodes of the cluster graph represent gland centroids. Method 400 also includes, at 450, defining pairwise spatial relationships between two or more glands in the subgraph. The edges of the localized subgraph between at least one pair of glands are defined by a probabilistic decaying function. In one embodiment, the probabilistic decaying function is a probabilistic decaying function of the Euclidean distance between gland centroids. Method 400 may also include, at 450, varying the density of the subgraph by varying the probability of connecting nodes. In another embodiment, the edges of the subgraph may be defined by a different probabilistic decaying function.

Method 400 also includes, at 460, controlling the computer to construct a directional gland tensor co-occurrence matrix based, at least in part, on the pairwise spatial relationships. Method 400 further includes, at 470, deriving second order statistical features from the directional gland tensor co-occurrence matrix. In one embodiment, the second order statistical features include entropy, homogeneity, energy, or correlation. In another embodiment, the second order statistical features may include other second order statistical features, including, but not limited to, contrast energy, contrast inverse moment, contrast average, contrast variance, contrast entropy, intensity average, intensity variance, and intensity entropy.

Method 400 also includes, at 480, controlling the computer to produce a BCR recurrence score based, at least in part, on the second order statistical features derived from the directional gland tensor co-occurrence matrix. In one embodiment, summed tensor co-occurrence matrices denote the frequency with which two glands of two directionalities co-occur. In another embodiment, a colormap of the gland subgraphs corresponds to the average intensity in each neighborhood. Producing an objective BCR recurrence score based, at least in part, on the second order statistical features derived from the directional gland tensor co-occurrence matrix provides a statistically significant improvement in accuracy compared to conventional QH.

Figure 5:
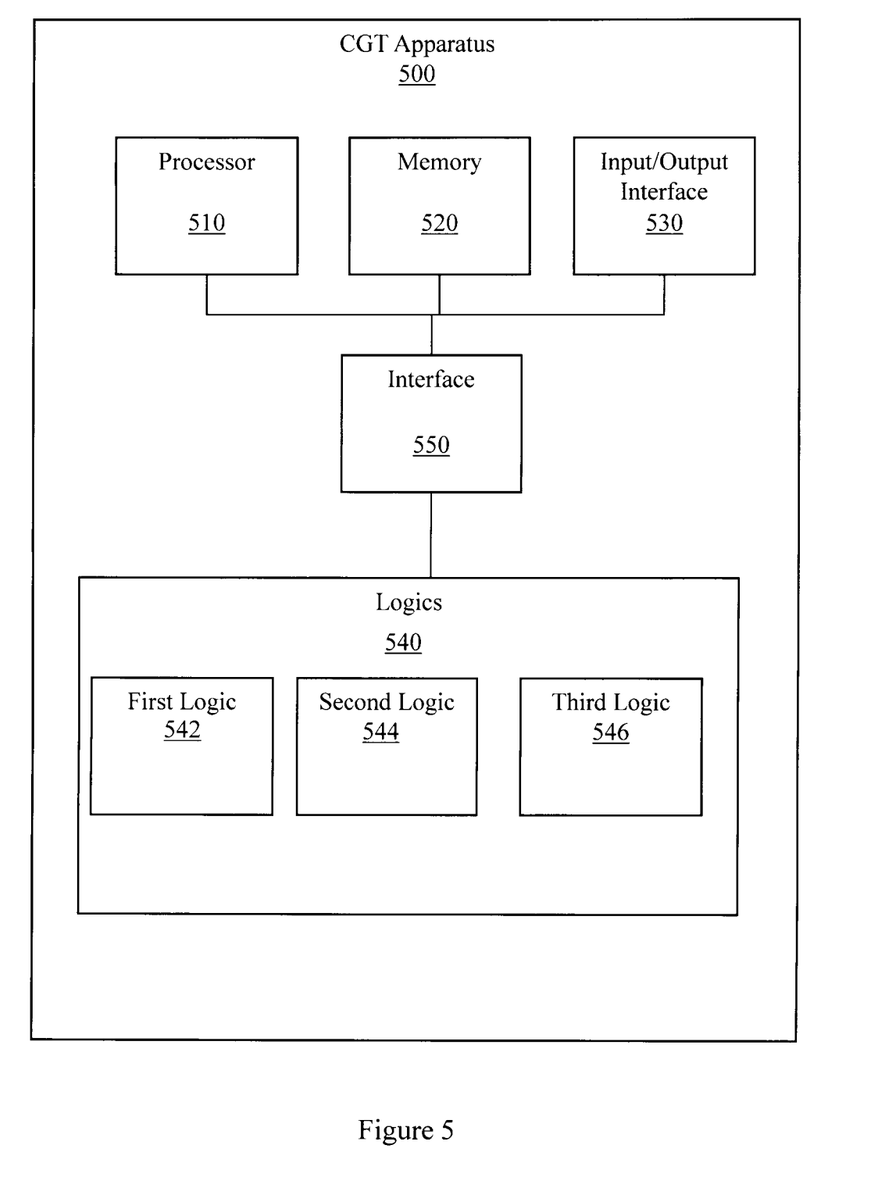
FIG. 5 illustrates an example apparatus that generates a risk of failure score for a material based on directional disorder.

FIG. 5 illustrates an example apparatus 500 for associating directional disorder with a risk of failure in a region of interest in a material. In one embodiment, the material may be a non-biological material. Apparatus 500 includes a processor 510, a memory 520, an input/output interface 530, a set of logics 540, and an interface 550. Interface 550 connects the processor 510, the memory 520, the input/output interface 530, and the set of logics 540.

The set of logics 540 associates directional disorder with a risk of failure in a region of interest in a material. The set of logics includes a first logic 542. First logic 542 detects a fundamental unit of composition in the region of interest. First logic 542 segments boundaries of the fundamental unit. In one embodiment, first logic 542 segments boundaries of the fundamental unit using automatic region growing to detect and segment boundaries. First logic 542 may also use a probabilistic pairwise Markov random field classifier to subsequently prune out boundaries that do not pertain to the fundamental unit of composition. In another embodiment, first logic 542 may use a different field classifier to prune boundaries.

The set of logics 540 includes a second logic 544 that constructs a sparsified localized subgraph from the detected and segmented fundamental units. Second logic 544 defines pairwise spatial relationships between the fundamental units in the subgraph. In one embodiment, second logic 544 uses a probabilistic decaying function to set the edges between the nodes of the subgraph. Second logic 544 constructs a directional tensor co-occurrence matrix based, at least in part, on the pairwise spatial relationships. In one embodiment, the nodes of the sparsified local subgraph represent the centroids of the fundamental units.

The set of logics 540 also includes a third logic 546 that derives second-order statistical features from the directional co-occurrence matrix. In one embodiment, the second-order statistical features include at least one of entropy, energy, homogeneity, and correlation. In other embodiments, logic 546 may derive other additional second-order statistical features, including but not limited to, contrast energy, contrast inverse moment, contrast average, contrast variance, contrast entropy, intensity average, intensity variance, or intensity entropy. One of ordinary skill in the art will appreciate that logic 546 may derive other second-order statistical features. Third logic 546 also produces a risk of failure score based, at least in part, on the second-order statistical features.

Figure 6:
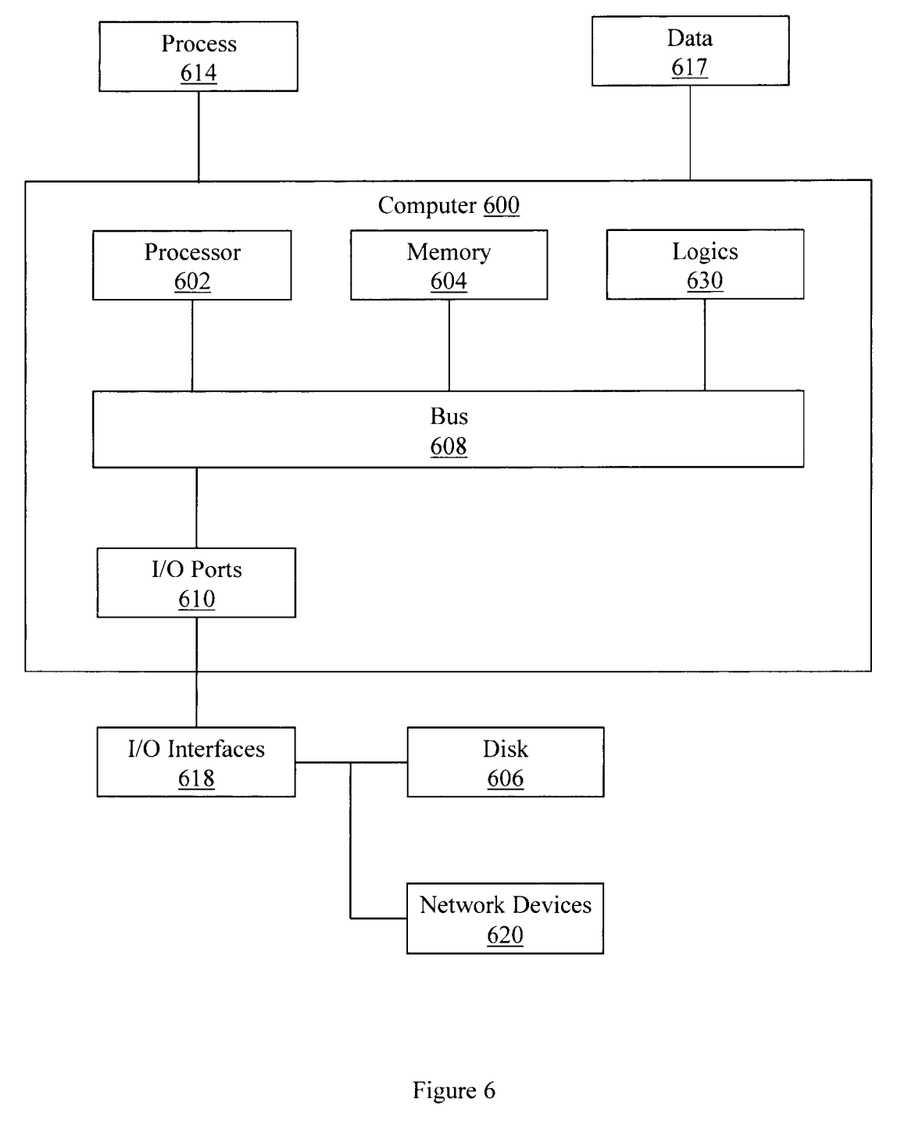
FIG. 6 illustrates an example computer in which example methods illustrated herein can operate.

FIG. 6 illustrates an example computer 600 in which example methods illustrated herein can operate and in which example logics may be implemented. In different examples computer 600 may be part of a digital whole slide scanner or may be operably connectable to a digital whole slide scanner.

Computer 600 includes a processor 602, a memory 604, and input/output ports 610 operably connected by a bus 608. In one example, computer 600 may include a set of logics 630 that is configured to perform a method of associating gland orientation disorder with malignancy and risk of post-surgical biochemical recurrence in a CaP patient. In another example, the set of logics 630 may control the computer 600 to compute a biochemical recurrence score for a cancer patient. Thus, the set of logics 630, whether implemented in computer 600 as hardware, firmware, software, and/or a combination thereof may provide means (e.g., hardware, software) for receiving digitized image data, means (e.g., hardware, software) for performing a method of associating gland orientation disorder with malignancy and risk of post-surgical biochemical recurrence in a CaP patient and means (e.g., hardware, software) for computing a biochemical recurrence score for a cancer patient. In different examples, the set of logics 630 may be permanently and/or removably attached to computer 600.

Processor 602 can be a variety of various processors including dual microprocessor and other multi-processor architectures. Memory 604 can include volatile memory and/or non-volatile memory. A disk 606 may be operably connected to computer 600 via, for example, an input/output interface (e.g., card, device) 618 and an input/output port 610. Disk 606 may include, but is not limited to, devices like a magnetic disk drive, a tape drive, a Zip drive, a flash memory card, and/or a memory stick. Furthermore, disk 606 may include optical drives like a CD-ROM and/or a digital video ROM drive (DVD ROM). Memory 604 can store processes 614 and/or data 616, for example. Disk 606 and/or memory 604 can store an operating system that controls and allocates resources of computer 600.

Bus 608 can be a single internal bus interconnect architecture and/or other bus or mesh architectures. While a single bus is illustrated, it is to be appreciated that computer 600 may communicate with various devices, logics, and peripherals using other busses that are not illustrated (e.g., PCIE, SATA, Infiniband, 1394, USB, Ethernet).

Computer 600 may interact with input/output devices via I/O interfaces 618 and input/output ports 610. Input/output devices can include, but are not limited to, digital whole slide scanners, a keyboard, a microphone, a pointing and selection device, cameras, video cards, displays, disk 606, network devices 620, and other devices. Input/output ports 610 can include but are not limited to, serial ports, parallel ports, and USB ports.

Computer 600 may operate in a network environment and thus may be connected to network devices 620 via I/O interfaces 618, and/or I/O ports 610. Through the network devices 620, computer 600 may interact with a network. Through the network, computer 600 may be logically connected to remote computers. The networks with which computer 600 may interact include, but are not limited to, a local area network (LAN), a wide area network (WAN), and other networks.

In one example, a method may be implemented as computer executable instructions. Thus, in one example, a computer-readable storage medium may store computer executable instructions that if executed by a machine (e.g., computer) cause the machine to perform methods described or claimed herein including method 100, method 200, and method 400. While executable instructions associated with the listed methods are described as being stored on a computer-readable storage medium, it is to be appreciated that executable instructions associated with other example methods described or claimed herein may also be stored on a computer-readable storage medium. In different embodiments the example methods described herein may be triggered in different ways. In one embodiment, a method may be triggered manually by a user. In another example, a method may be triggered automatically.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage medium", as used herein, refers to a medium that stores instructions or data. "Computer-readable storage medium" does not refer to propagated signals. A computer-readable storage medium may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage medium may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Logic", as used herein, includes but is not limited to hardware, firmware, software in execution on a machine, or combinations of each to perform a function(s) or an action(s), or to cause a function or action from another logic, method, or system. Logic may include a software controlled microprocessor, a discrete logic (e.g., ASIC), an analog circuit, a digital circuit, a programmed logic device, a memory device containing instructions, and other physical devices. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, ABC, AAA, AAB, AABB, AABBC, AABBCC, (e.g., the data store may store only A, only B, only C, A&B, A&C, B&C, A&B&C, A&A&A, A&A&B, A&A&B&B, A&A&B&B&C, A&A&B&B&C&C). It is not intended to require one of A, one of B, and one of C. When the applicants intend to indicate "at least one of A, at least one of B, and at least one of C", then the phrasing "at least one of A, at least one of B, and at least one of C" will be employed.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage medium storing computer executable instructions that when executed by a computer cause the computer to perform a method of associating gland orientation disorder with malignancy and risk of post-surgical biochemical recurrence (BCR) in a prostate cancer (CaP) patient, the method comprising:
   accessing a digitized image of a section of a prostate demonstrating pathology associated with CaP in the patient;
   detecting a gland in a region of interest of the digitized image;
   segmenting an individual gland boundary in the region of interest in the digitized image into a set of gland boundary points;
   producing a gland tensor by associating a tensor with the gland, where the gland tensor indicates the dominant orientation of the gland, and where the gland tensor is based on the major axis of the gland;
   constructing a subgraph of a localized gland network within the region of interest, where constructing the subgraph comprises linking individual glands located proximal to each other into the localized gland network, where the nodes of the subgraph represent individual gland centroids, and where the edges of the subgraph are defined between pairs of glands by a probabilistic decaying function;

constructing a tensor co-occurrence matrix, where elements of the tensor co-occurrence matrix comprise gland tensor pairs, where the gland tensor pairs are defined by the subgraph, and where the tensor co-occurrence matrix aggregates co-occurring gland tensors based, at least in part, on the frequency with which orientations of two individual glands located proximal to each other co-occur;

deriving second-order statistics of gland orientations in the localized gland networks in the digitized image;

selectively differentiating a cancerous tissue region from a non-cancerous tissue region in the image based, at least in part, on the second-order statistics; and establishing a BCR score for the patient based, at least in part, on the second-order statistics.

2. The non-transitory computer-readable storage medium of claim 1, where detecting a gland and segmenting an individual gland boundary comprises controlling the computer to:

access a color space luminance channel image of the region of interest, where glands in the color space luminance channel image appear as contiguous, high intensity pixel regions;

produce a convolved luminance image by convolving the color space luminance channel image with a Gaussian kernel;

detect a seed pixel corresponding to a peak intensity in the convolved luminance image, where the seed pixel represents a current region (CR);

initialize a bounding box around the seed pixel;

denote eight connected pixels surrounding the seed pixel as a current boundary (CB);

produce a removed CB pixel by removing the pixel in the CB with the highest intensity from the CB, and upon determining that the removed CB pixel is not outside the bounding box:

controlling the computer to incorporate the removed CB pixel into the CR as a new CR pixel;

incorporate the eight connected pixels surrounding the new CR pixel not already in the CR into the CB;

define an internal boundary (IB) as all CR pixels adjacent to the CB, and define a boundary strength as the mean intensity of the pixels in the IB minus the mean intensity of the pixels in the CB.

3. The non-transitory computer-readable storage medium of claim 2, the method comprising defining an optimal region as the CR where the maximum boundary strength is achieved.

4. The non-transitory computer-readable storage medium of claim 1, the method comprising using a probabilistic pairwise Markov random field classifier to remove a non-gland boundary in the region of interest.

5. The non-transitory computer-readable storage medium of claim 1, the method comprising obtaining the dominant orientation of the gland through principal component analysis (PCA) of the set of gland boundary points, where the first principal component describes the directionality of the gland in the form of the major axis, where the greatest variance in the gland boundary occurs along the major axis.

6. The non-transitory computer-readable storage medium of claim 5, the method comprising converting the major axis to an angle counterclockwise from a positive horizontal axis.

7. The non-transitory computer-readable storage medium of claim 1, where the subgraph is a sparsified graph, where the sparsified graph defines a pairwise spatial relationship between glands, and where the contributions of stromal regions in the region of interest are minimized by preventing edges in the sparsified graph from traversing heterogeneous tissues including stroma and epithelium.

8. The non-transitory computer-readable storage medium of claim 1, where the probabilistic decaying function is a probabilistic decaying function of the Euclidean distance between gland centroids.

9. The non-transitory computer-readable storage medium of claim 1, where the density of the subgraph is controlled by a randomly generated value V from 0.0 through infinity, where 0 represents a high probability of connecting nodes, and infinity represents a low probability of connecting nodes, V being a real number.

10. The non-transitory computer-readable storage medium of claim 1, the method comprising discretizing gland orientations in angular bins following conversion of the major axis to an angle counterclockwise from a positive horizontal axis.

11. The non-transitory computer-readable storage medium of claim 1, where the second-order statistics comprise at least one of entropy, homogeneity, energy, correlation, contrast energy, contrast inverse moment, contrast average, contrast variance, contrast entropy, intensity average, intensity variance, and intensity entropy.

12. The non-transitory computer-readable storage medium of claim 1, the method comprising differentiating the cancerous tissue region and the non-cancerous tissue region as a function of the disorganization of the gland orientation.

13. The non-transitory computer-readable storage medium of claim 2, where the color space luminance channel image is a Commission internationale de l'éclairage L*a*b* (CIELAB) image.

14. A method for controlling a computer to compute a biochemical recurrence (BCR) score for a cancer patient, comprising:

detecting a gland in a region of interest of a digitized histopathology section associated with the cancer patient;

segmenting gland boundaries of the gland into a set of gland boundaries;

calculating a directional gland tensor for the gland;

constructing a localized subgraph of a gland network in the region of interest;

defining pairwise spatial relationships between two or more glands in the subgraph;

constructing a directional gland tensor co-occurrence matrix based, at least in part, on the pairwise spatial relationships;

deriving second order statistical features from the directional gland tensor co-occurrence matrix; and controlling the computer to produce a BCR recurrence score based, at least in part, on the second order statistical features, where the BCR recurrence score predicts BCR with at least 66% accuracy.

15. The method of claim 14, comprising:

detecting the gland using automatic region growing; and segmenting the gland boundaries using automatic region growing.

16. The method of claim 14, comprising calculating the directional gland tensor from a principal component analysis (PCA) of the set of gland boundaries.

17. The method of claim 14, where the localized subgraph is a cluster graph, and where the nodes of the localized subgraph represent gland centroids.

18. The method of claim 14, where the edges of the localized subgraph between at least one pair of glands are defined by a probabilistic decaying function, where the probabilistic decaying function minimizes the contributions of stromal regions in the region of interest by preventing edges of the subgraph from traversing heterogeneous tissues including stroma and epithelium.

19. The method of claim 14, where the second order statistical features include at least one of entropy, homogeneity, energy, and correlation.

20. The method of claim 19, where entropy is defined as $\Sigma_{\theta_1,\theta_2} -C(\theta_1,\theta_2,)\log(C(\theta_1,\theta_2)))$ where $\theta_1$ is a directional gland tensor for a first gland in a pair of glands, where the pair of glands is in the localized subgraph, where $\theta_2$ is a directional gland tensor for a second gland in the pair of glands, and where C is the directional gland tensor co-occurrence matrix, where the directional gland tensor co-occurrence matrix is a b×b co-occurrence matrix.

21. The method of claim 19, where homogeneity is defined as $$\Sigma_{\theta_1,\theta_2} \frac{C(\theta_1, \theta_2)}{1+|\theta_1-\theta_2|}$$

where $\theta_1$ is a directional gland tensor for a first gland in a pair of glands, where the pair of glands is in the localized subgraph, where $\theta_2$ is a directional gland tensor for a second gland in the pair of glands, and where C is the directional gland tensor co-occurrence matrix, where the directional gland tensor co-occurrence matrix is a b×b co-occurrence matrix.

22. The method of claim 19, where energy is defined as $\Sigma_{\theta_1,\theta_2} C(\theta_1,\theta_2)^2$ where $\theta_1$ is a directional gland tensor for a first gland in a pair of glands, where the pair of glands is in the localized subgraph, where $\theta_2$ is a directional gland tensor for a second gland in the pair of glands, and where C is the directional gland tensor co-occurrence matrix, where the directional gland tensor co-occurrence matrix is a b×b co-occurrence matrix.

23. The method of claim 19, where correlation is defined as $$\Sigma_{\theta_1,\theta_2} \frac{(\theta_1-\mu\theta_1)(\theta_2-\mu\theta_2)C(\theta_1,\theta_2)}{\sigma_{\theta_1},\sigma_{\theta_2}}$$

where $\theta_1$ is a directional gland tensor for a first gland in a pair of glands, where the pair of glands is in the localized subgraph, where $\theta_2$ is a directional gland tensor for a second gland in the pair of glands, and where C is the directional gland tensor co-occurrence matrix, where the directional gland tensor co-occurrence matrix is a b×b co-occurrence matrix.

24. An apparatus, comprising:
a processor;
a memory;
an input/output interface;
a set of logics that associate directional disorder with a risk of failure in a region of interest in a material, and
an interface to connect the processor, the memory, the input/output interface and the set of logics,
the set of logics comprising:
a first logic that detects a fundamental unit of composition in the region of interest, segments boundaries of the fundamental unit, and calculates a tensor for the fundamental unit, where the tensor indicates the dominant orientation of the fundamental unit;
a second logic that constructs a sparsified localized subgraph from the detected fundamental units, defines pairwise spatial relationships between the fundamental units in the subgraph, and constructs a directional tensor co-occurrence matrix based, at least in part on the pairwise spatial relationships, where the nodes of the sparsified localized subgraph represent the centroids of the fundamental unit; and
a third logic that derives second order statistical features from the directional tensor co-occurrence matrix, and produces a risk of failure score based, at least in part, on the second order statistical features.

* * * * *